(12) United States Patent
Kurtz, Jr.

(10) Patent No.: US 9,346,855 B2
(45) Date of Patent: May 24, 2016

(54) PROTEIN SCAFFOLDS FOR TARGETED DELIVERY OF TOXIC IRON TO CANCER CELLS

(71) Applicant: Board of Regents of the University of Texas System, Austin, TX (US)

(72) Inventor: Donald M. Kurtz, Jr., Helotes, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/626,393

(22) Filed: Sep. 25, 2012

(65) Prior Publication Data

US 2013/0090293 A1 Apr. 11, 2013

Related U.S. Application Data

(60) Provisional application No. 61/539,840, filed on Sep. 27, 2011.

(51) Int. Cl.
| | |
|---|---|
| C07K 14/00 | (2006.01) |
| C07K 7/06 | (2006.01) |
| C07K 14/795 | (2006.01) |
| C07K 16/00 | (2006.01) |

(52) U.S. Cl.
CPC . *C07K 14/00* (2013.01); *C07K 7/06* (2013.01); *C07K 14/795* (2013.01); *C07K 16/00* (2013.01)

(58) Field of Classification Search
None
See application file for complete search history.

(56) References Cited

U.S. PATENT DOCUMENTS

2007/0258889 A1* 11/2007 Douglas et al. .............. 424/1.37

OTHER PUBLICATIONS

Wongsinkongman et al., Bioorganic & Medicinal Chemistry, 2002, 10:583-591.*
The Porphyrin Handbook, vol. 8, Electron Transfer, Edited by Kadish et al., 2000, pp. 90-91, 132-133.*
Baaghil et al. "Core formation in *Escherichia coli* bacterioferritin requires a functional ferroxidase center." (2003). Biochemistry 42, 14047-14056. (Abstract).
Conlan et al. "Photo-catalytic oxidation of a di-nuclear manganese centre in an engineered bacterioferritin 'reaction centre'." (2009) Biochim. Biophys. Acta 1787, 1112-1121.
Deutscher "Phage display in molecular imaging and diagnosis of cancer." (2010) Chem. Rev. 110, 3196-3211.
Garg et al. "A [2Fe—2S] protein encoded by an open reading frame upstream of the *Escherichia coli* bacterioferritin gene." (1996) Biochemistry 35, 6297-6301. (Abstract).
Imlay "Pathways of oxidative damage." (2003) Annu. Rev. Microbiol. 57, 395-418. (Abstract).
Komatsu et al. "Photosensitized reduction of water to hydrogen using human serum albumin complexed with zinc-protoporphyrin IX." (2006) J. Am. Chem. Soc. 128, 16297-16301.
Lee et al. "High-level production of heme-containing holoproteins in *Escherichia coli*." (2001) Appl. Microbiol. Biotechnol. 55, 187-191.
Matsuo et al. "Photocatalytic hydrogen generation using a protein-coated photosensitizer with anionic patches and a monocationic electron mediator." (2008) Chem. Commun., 3684-3686. (Abstract).
Park et al. "Substantial DNA damage from submicromolar intracellular hydrogen peroxide detected in Hpx-mutants of *Escherichia coli*." Proc. Natl. Acad. Sci. U.S.A. 102, 9317-9322, 2005.
Trachootham et al. "Targeting cancer cells by ROS-mediated mechanisms: a radical therapeutic approach?" (2009) Nat. Rev. Drug Discov. 8, 579-591. (Abstract).
Uchida et al. "Targeting of cancer cells with ferrimagnetic ferritin cage nanoparticles." (2006) J. Am. Chem. Soc. 128, 16626-16633. (Abstract).
Varnado et al. "System for the expression of recombinant hemoproteins in *Escherichia coli*." (2004) Protein Expression Purif. 35, 76-83.(Abstract).
Watt et al. "Redox properties and Mossbauer-spectroscopy of Azotobacter-vnelandii bacterioferritin." (1986) Biochemistry 25, 4330-4336. (Abstract).
Weeratunga et al. "Binding of Pseudomonas aeruginosa apobacterioferritin-associated ferredoxin to bacterioferritin B promotes heme mediation of electron delivery and mobilization of core mineral Iron." (2009) Biochemistry 48, 7420-7431. (Abstract).

* cited by examiner

*Primary Examiner* — Hong Sang
(74) *Attorney, Agent, or Firm* — Meyertons, Hood, Kivlin, Kowert & Goetzel, P.C.; Eric B. Meyertons

(57) ABSTRACT

Described herein are modifications and adaptations of iron storage proteins for a novel photo-initiated approach to cancer therapy whereby cells are killed via production of iron-generated hydroxyl radicals. The iron is photo-released from a protein scaffold that includes tumor-targeting peptides and/or proteins fused to the exterior surface of the protein scaffold. One or more photosensitizers are coupled to the protein shell. The multiple tumor-targeting peptides and/or proteins will bind to specific hyperexpressed receptors on the cancer cells. After binding of the photosensitizer-iron-loaded protein to the cancer cells, photochemical excitation of the photosensitizers with tissue-penetrating near-infrared light triggers release of "free" ferrous iron, which in oxic or mildly hypoxic intracellular environments generates toxic hydroxyl radicals via Fenton chemistry. This light-triggered release of "free" iron overwhelms the cancer cells' defenses against free radicals. The combination of tumor-targeting peptides and photo-triggered release of iron ensures that non-cancerous cells are not bombarded with iron.

8 Claims, 4 Drawing Sheets

PROTEIN SCAFFOLDS FOR TARGETED DELIVERY OF TOXIC IRON TO CANCER CELLS

PRIORITY CLAIM

This application claims priority to U.S. Provisional Application Ser. No. 61/539,840 entitled "PROTEIN SCAFFOLDS FOR TARGETED DELIVERY OF TOXIC IRON TO CANCER CELLS" filed Sep. 27, 2011, which is incorporated herein by reference in its entirety.

BACKGROUND OF THE INVENTION

1. Field of the Invention

The invention generally relates to compounds, compositions and methods for the treatment of cancerous cells. More specifically, the invention relates compounds, compositions and methods for iron-based cancer photodynamic therapy.

2. Description of the Relevant Art

Exogenous agents that rapidly elevate reactive oxygen species (ROS) above toxic threshold levels has been touted as a potentially effective, but largely untested cancer therapeutic strategy.

"Free" ferrous iron is known to produce cell-damaging ROS, principally hydroxyl radical, via the Fenton reaction in which hydrogen peroxide produced as a byproduct of oxygen metabolism is one-electron reduced by $Fe^{2+}$. The Fenton-derived hydroxyl radicals damage lipids, proteins and DNA even at sub-micromolar steady-state levels of hydrogen peroxide and free iron. The $Fe^{3+}$ product of the Fenton reaction is rapidly re-reduced to $Fe^{2+}$ by intracellular reductants, so that this Fenton generation of hydroxyl radical is catalytic.

One rationale for the limited effectiveness of singlet oxygen photodynamic therapy is that it requires well-oxygenated tissues, whereas many tumor environments tend to be hypoxic. Intracellular Fenton chemistry, on the other hand, occurs at toxic levels even under hypoxic conditions at relatively low (micromolar or lower) levels of hydrogen peroxide and "free" iron. Furthermore, hypoxia results in a relatively reducing environment, which would facilitate the catalytic Fenton chemistry mentioned above. Iron and hydrogen peroxide are relatively small "drugs" and could conceivably penetrate the interior of solid tumors more efficiently than traditional "small molecule" organic drugs.

Published tumor targeting methods typically use antibodies to tumor cell surface proteins or so-called tumor-targeting peptides (TTPs), which bind to specific cell surface receptors that are often hyperexpressed in tumors. Numerous TTPs have been reported. Particles containing multiple tumor targeting moieties have been shown to be more effective as tumor selective agents than the corresponding monomers.

SUMMARY OF THE INVENTION

A compound capable of selectively targeting tumor cells is composed of a protein scaffold; one or more tumor targeting peptides and/or proteins coupled to an outer surface of the protein scaffold, wherein the tumor targeting peptides and/or proteins bind to predetermined cell surface receptors of tumor cells; one or more iron-containing molecules disposed in a core of the protein scaffold; and one or more photosensitizing molecules coupled to the protein scaffold.

In some embodiments, the protein scaffold may be bacterioferritin. The tumor targeting peptides and/or proteins attached to the protein scaffold have the structure CDCRGDCFC (SEQ ID NO. 1). Tumor targeting proteins and/or peptides may target breast cancer cells or prostate cancer cells. The iron containing, in some embodiments, may be is ferric-oxyhydroxide polymer.

Tumor targeting proteins and/or peptides may target breast cancer cells or prostate cancer cells. The iron containing, in some embodiments, may be is ferric-oxyhydroxide polymer.

The photosensitizing molecules may be sensitive to different types of activating light. In some embodiments, the photosensitizing molecules are sensitive to infrared irradiation.

The compound capable of selectively targeting tumor cells may be used to treat cancer in a subject by administering to the subject who would benefit from such treatment a therapeutically effective amount of the tumor selective compound.

In another embodiment, the compound capable of selectively targeting tumor cells may be used to detect cancerous cells. In an exemplary procedure, cells obtained from a subject may be contacted with the tumor selective compound. Activating light may be applied to the contacted cells. The protein scaffold containing the tumor targeting peptides and/or proteins and the photosensitizing molecules contacting the cells produces a detectable signal, in the presence of the activating light, that indicates the presence of a cancerous cell.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
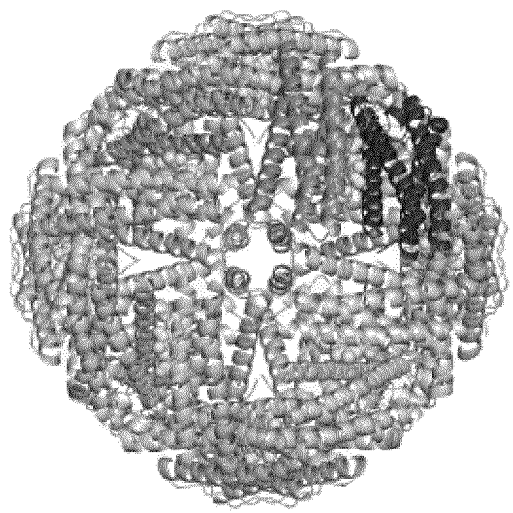
FIG. 1 depicts a representation of the 24-subunit Bfr with one of the twelve heme-bridged subunit pairs highlighted in blue and green.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

In one embodiment, a compound capable of photo-triggered release of Fenton-reactive iron, comprises: an iron source; one or more tumor targeting peptides and/or proteins; and photosensitizing molecules, coupled to a protein scaffold. A protein scaffold includes one or more tumor targeting peptides and/or proteins ("TTPs") on its outer surface and photosensitizing molecules in the walls. A hollow interior cavity of the protein scaffold includes an iron source. The tumor targeting peptides and/or proteins on the outer surface of the protein scaffold are selected to bind to specific receptors on the cancer cells. The photosensitizers in the protein, upon irradiation with tissue penetrating near infrared light, trigger the release of "free" iron, which diffuse to the cancer cell surface. The iron loaded protein scaffold is, thus, able to send iron into the cancer cell when irradiated. Free iron is highly toxic to cells because it produces free radicals. The tumor targeting peptides and/or proteins ensure that only cancer cells and not normal cells are bombarded with iron, the release of which occurs only upon irradiation.

Figure 2:
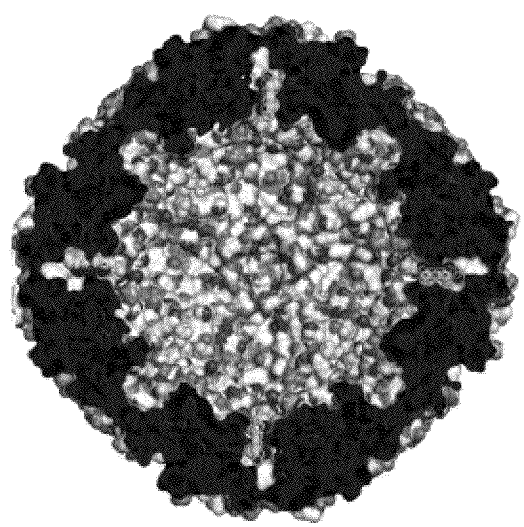
FIG. 2 depicts a cross-sectional view of the 24-subunit Bfr showing the ~8-nm interior cavity and hemes embedded within the protein shell.
Figure 3:
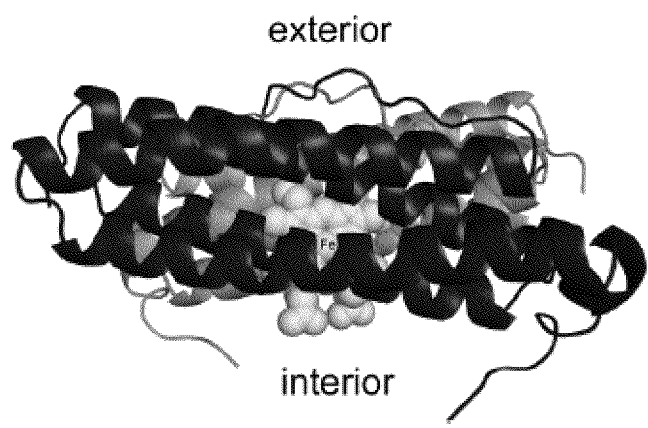
FIG. 3 depicts a representation of a heme-bridged dimer.
Figure 4:
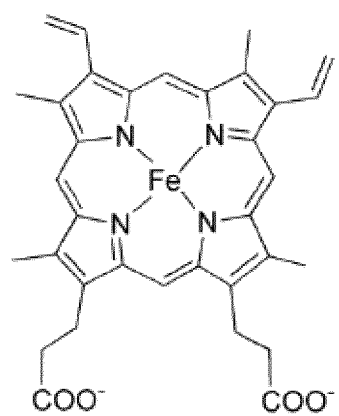
FIG. 4 depicts the chemical structure of heme oriented same as the heme in FIG. 3.
Figure 5:
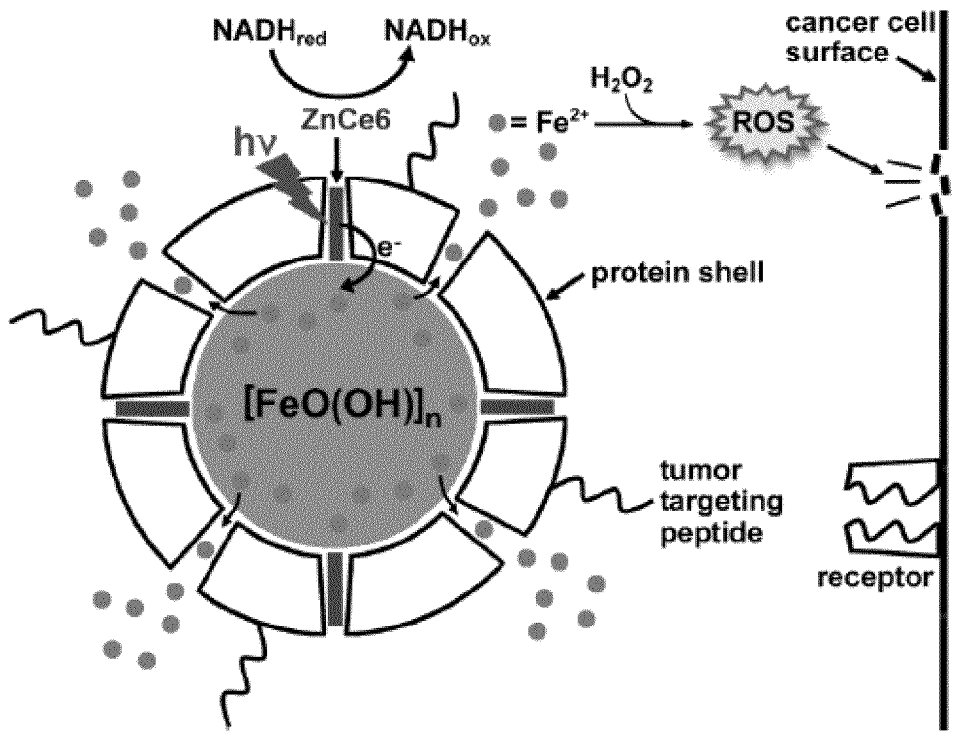
FIG. 5 depicts a schematic diagram of a tumor selective compound.
Figure 6:
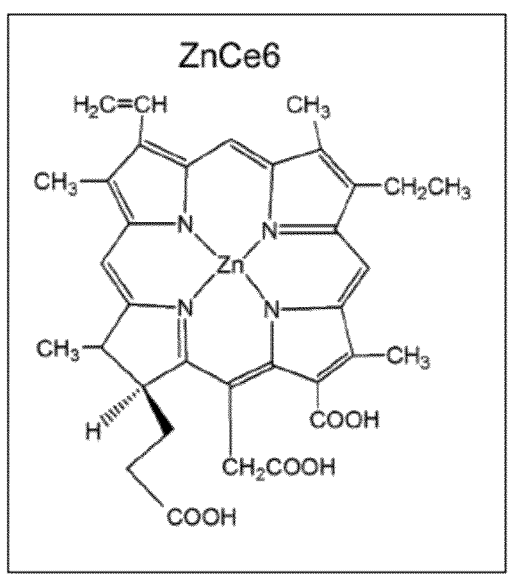
FIG. 6 depicts the chemical structure of ZnCe6.

In an embodiment, the protein scaffold is an iron-storage protein called bacterioferritin (Bfr), which can sequester up to 3,000 iron atoms, in the form of ferric-oxyhydroxide polymer ($[FeO(OH)]_n$ ($n \leq 3,000$)) in its interior cavity. Bfr also is capable of binding 12 heme groups in its protein shell surrounding the iron core. Relevant structural features of Bfr are shown in FIGS. 1-4. FIG. 1 Cartoon representation of the 24-subunit Bfr with one of the twelve heme-bridged subunit pairs highlighted in blue and green. Hemes are highlighted in yellow. FIG. 2 depicts a slice through of the 24-mer showing an ~8-nm interior cavity and hemes embedded within the protein shell. FIG. 3 depicts a cartoon representation of a heme-bridged dimer. FIG. 4 depicts a schematic structure of heme oriented same as the heme in FIG. 3. FIG. 5 depicts a schematic diagram of a modified protein scaffold and the mechanism of action. FIG. 6 depicts the structure of Zn-chlorin e6 (ZnCe6).

In one embodiment, Bfr is used as the protein scaffold. Bfr includes 12 heme groups, as shown in FIG. 1. In an embodiment, the 12 hemes in Bfr are replaced with photosensitizing structural homologues, such as Zn-protoporphyrin IX (ZnPPIX) and Zn-chlorin e6 (ZnCe6). The structure of ZnPPIX is identical to that of heme (FIG. 4), except that it contains zinc in place of iron. ZnPPIX or ZnCe6 are essentially irreversibly bound at the same sites where heme binds in the native Bfr scaffold (FIG. 1). The modified protein thus, comprises a Bfr protein cage containing 24 TTPs, 12 ZnPPIXs or ZnCe6s, and up to 3,000 iron atoms ([ZnPPIX or $ZnCe6_{12}$-$TTP_{24}$-$Fe_{\leq 3000}$-Bfr]). Photo-irradiation of ZnPPIX or ZnCe6 generates the reducing ZnCe6 triplet excited state. The ZnPPIX or ZnCe6 excited triplet state is thermodynamically capable of reducing the ($[FeO(OH)]_n$ core (orange sphere in FIG. 5 either directly or via di-iron "ferroxidase centers" (not shown in FIG. 5) located adjacent to the heme binding sites within each subunit. This photochemical redox process produces ferrous iron (blue spheres in FIG. 5) and the oxidized form of ZnPPIX ($ZnPPIX^{+\cdot}$) or ZnCe6 ($ZnCe6^{+\cdot}$). The ferrous iron diffuses out through numerous pores in the protein shell, and the highly oxidizing $ZnPPIX^{+\cdot}$ or $ZnCe6^{+\cdot}$ is reduced back to ZnPPIX or ZnCe6 by tumor-endogenous reducing agents, such as NADH, functioning as sacrificial electron donors. The initial photo-oxidized products of the sacrificial electron donors typically undergo radical chain reactions and rearrangements, rendering the net photochemical redox reactions irreversible.

The data provided below uses ZnPPIX as a test case to demonstrate feasibility of the invention. ZnCe6 has absorptions in the tissue-penetrating near infra-red (near-IR) region,[22] which is advantageous for in vivo applications. The ZnCe6 fluorescence ($\lambda_{em}$ ~650 nm) simultaneously provides a means to use imaging probes to confirm that the compound has targeted cancer cells.

ZnPPIX or ZnCe6 are essentially irreversibly bound at the same sites where heme binds in the native Bfr scaffold (FIG. 1). The irreversible binding of the photosensitizers minimizes the possibility of adventitious, non-specific photochemical damage. The widely separated binding sites for the individual photosensitizer molecules within the protein scaffold inhibits self-quenching of the photochemistry. The proximity of bound ZnPPIX or ZnCe6 to the $[FeO(OH)]_n$ core facilitates electron transfer over singlet $O_2$ generation. The photochemical redox cycle of [$ZnCe6_{12}$-$TTP_{24}$-$Fe_{\leq 3000}$-Bfr], thus, generates a tumor-localized flux of "free" ferrous iron ($Fe^{2+}$) greatly exceeding the normal steady state levels of tissue or intracellular free iron. The intracellular components involved in iron reduction and release from Bfr in bacteria are not well understood, but are thought to involve the heme. Since Bfr is found exclusively in bacteria, and heme-containing ferritins are not known to exist in eukaryotes, Bfr-specific iron-releasing components are unlikely to be present in mammalian cells. Therefore, significant iron release from tumor-targeted Bfr is unlikely to occur in the absence of photoexcitation.

Embodiments include fusion of a TTP to the Bfr subunit amino (N)-terminus of [ZnPPIX- or $ZnCe6_{12}$-$TTP_{24}$-$Fe_{\leq 3000}$-Bfr]. The N-terminal ends of all 24 Bfr protein subunits are exposed on the outer surface of the protein shell. We routinely isolate Bfr without the need for an affinity tag. Therefore, TTPs added to the Bfr N-terminus do not interfere with Bfr isolation and purification. However, an N-terminal His-tag has been engineered onto E. coli Bfr by others, and this tag did not disrupt the 24-mer structure or iron uptake. The His-tagged Bfr was found to bind to the affinity resin used for its purification. This latter observation constitutes a precedent for Bfr N-terminal peptide/receptor interaction. A nine-residue peptide which selectively binds $\alpha_v\beta_3$ integrins, which are known to be upregulated on tumor vasculature, was added to the N-terminus of a related human iron storage protein called ferritin, and this modified ferritin was found to bind to a cancer cell line.

A TTP may be added to a protein scaffold using exposed amino (N)-terminus. For example, in Bfr the N-terminal ends of all 24 Bfr protein subunits are exposed on the outer surface of the protein shell. Standard molecular biology procedures may be used to attach TTPs to the Bfr N-terminus. In one embodiment, the targeting peptide, CDCRGDCFC (SEQ ID No. 1, listed using the standard one-letter acronyms for amino acid residues) is used as a TTP. This targeting peptide is known to target $\alpha_v\beta_3$ integrins, which are up-regulated in tumor vasculature. In some embodiments, a three-glycine spacer is added to the C-terminus of this targeting peptide, thereby connecting it to the third residue at the N-terminal end of Bfr. The first two N-terminal residues of Bfr (MK) are added to the N-terminus of the targeting peptide. The twenty-four TTPs (one from each subunit) project from the outer surface of the protein cage, thereby providing a molecular attachment for tumor cell surface receptors. These externally attached TTPs did not affect iron loading of the internal cavity of the protein scaffold. Loading with iron atoms (e.g., ~3,000 iron atoms) results in an electron dense iron core, which may be imaged by transmission electron microscopy (TEM) to confirm binding to cancer cells.

White or wavelength-filtered light irradiation at varying intensities is accomplished using a commercially available non-laser light source. In vitro photochemical release of ferrous iron may be monitored by standard colorimetric methods, and production of Fenton-derived hydroxyl radical may be monitored by EPR spin trapping. The irradiation experiments may be conducted in pH 7 phosphate buffer either aerobically or anaerobically ($N_2$ atmosphere), as well as at sub-aerobic $O_2$ partial pressures and in the presence or absence of hydrogen peroxide in order to mimic a range of intracellular conditions. A common tumor-endogenous source of reducing equivalents, NADH is used as the "sacrificial electron donor" (FIG. 5). An alternative tumor-endogenous reducing agent, cysteine, may also be used. Neither of these intracellular reducing agents is known to directly reduce the $[FeO(OH)]_n$ core of Bfr in the absence of photoexcitation. In some embodiments, laser-light irradiation may be used to release iron from $[ZnCe6_{12}\text{-}TTP_{24}\text{-}Fe_{\leq 3000}\text{-}Bfr]$.

Binding of $[ZnPPIX$ or $ZnCe6_{12}\text{-}TTP_{24}\text{-}Fe_{\leq 3000}\text{-}Bfr]$ to C32 cancer cells was analyzed by visualization of the electron dense iron cores[25] by transmission electron microscopy and visualization of the ZnPPIX- or ZnCe6-Bfr by confocal fluorescence microscopy. In some embodiments, the isolated (i.e., no artificial iron loading) construct for intracellular fluorescence imaging may be used (because the $FeO(OH)]_n$ core may quench the ZnPPIX or ZnCe6 fluorescence). Decreases in cancer cell viability upon exposure to [ZnPPIX- or $ZnCe6_{12}\text{-}TTP_{24}\text{-}Fe_{\leq 3000}\text{-}Bfr]$ and visible/near-IR irradiation may be monitored using a standard colorimetric assay in microplates. The sacrificial reducing agents NAD(P)H and cysteine are typically present in the culture media or added. Since tumor environments are often hypoxic, a $CO_2$ cell culture incubator having the capability of controlling $O_2$ levels from ambient to 1% of ambient is used. This strategy can correlate $O_2$ levels with cell killing. Electron transfer to the $[FeO(OH)]_n$ core is the predominant quencher of the photoexcited ZnPPIX or ZnCe6, but it is also believed that singlet $O_2$ is formed to provide a "double whammy" for cell killing.

The compounds and methods described herein combine the strategies of photo-triggered release of Fenton-reactive iron with multiple tumor-targeting peptides and/or proteins using a protein nanoparticle scaffold, (e.g., Bfr). Unlike Bfr, mammalian ferritins do not contain heme (or any cofactor other than non-heme iron), and, therefore, are not useful for the photosensitized iron release approach proposed here. Protein scaffolds have not been reported as iron-releasing agents for cancer therapy. The photo-triggered release of massive doses of ferrous iron as a cancer therapy described herein is also unprecedented.

Other photosensitizing porphyrins chlorins, pheophorbides, as well as other approximately planar photosensitizers of size and shape similar to those of porphyrins, and which have absorptions in the near-IR region, such as phthalocyanines may be used as the photosensitizing molecules. Substitutions may also be made of amino acid residues lining the interior cavity of Bfr and the exit pores for the photo-reduced ferrous iron as needed to optimize iron release rates. Other peptides or proteins targeting specific types of cancers (e.g., peptides that target breast cancer, prostate cancer, etc.) may be coupled to the outer surface of the Bfr protein shell. Spacer residues may be optionally added to the peptides or proteins if necessary to improve tumor targeting. Chemically modifiable residues such as cysteine may also be added to the outer surface of the protein shell for attachment of agents, such as polyethylene glycol to shield the protein from the immune system. Embodiments, also include the use of Bfrs from other bacteria for optimization of photosensitizer attachment as well as iron incorporation and release.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

*E. coli* Bfr is unusually stable. Fifty milligrams of Bfr may be produced from a few liters of *E. coli* culture using standard protein overexpression and purification protocols. Published procedures were used for iron-loading (e.g., Baaghil et al. (2003) "Core formation in *Escherichia coli* bacterioferritin requires a functional ferroxidase center." *Biochemistry* 42, 14047-14056) and for incorporation of ZnPPIX or ZnCe6 into Bfr (e.g., Conlan et al. (2009) "Photo-catalytic oxidation of a di-nuclear manganese centre in an engineered bacterioferritin 'reaction centre'." *Biochim. Biophys. Acta* 1787, 1112-1121). Efficient ZnPPIX or ZnCe6 insertion into Bfr in place of heme was accomplished by using an *E. coli* strain overexpressing a heme receptor, ChuA. (See e.g., Lee et al. (2001). "High-level production of heme-containing holoproteins in *Escherichia coli*." *Appl. Microbiol. Biotechnol.* 55, 187-191; and Varnado et al. (2004). "System for the expression of recombinant hemoproteins in *Escherichia coli*." *Protein Expression Purif.* 35, 76-83. *E. coli* BL21(DE3) previously transformed with the *E. coli* Bfr expression plasmid is grown overnight in standard Luria-Bertani/ampicillin media (LB/amp). This strain is then transformed with Goodwin's pHEPX2.2, which expresses ChuA and tetracycline resistance. This transformation mixture is spread on agar plates with 20 µg/mL tetracycline. Colonies are selected which contain both the Bfr expression plasmid and pHEPX2.2. The resulting *E. coli* BL21(DE3)/Bfr/pHPEX2.2 strain is then cultured in 50-mL to 1-L batches of LB/amp at 37° C. When the cultures reach OD600 ~0.8, ~7 mg ZnPPIX or ZnCe6 (purchased from Frontier Scientific, Inc.) from a DMSO stock solution is added per liter of culture followed immediately by standard isopropyl-beta-D-thiogalactoside induction of protein expression. After 4 hours, the cells are harvested. The cells are subsequently lysed, and the ZnPPIX- or ZnCe6-Bfr are purified by standard ion-exchange and size-exclusion chromatographies. Loading of ZnPPIX or ZnCe6 using this procedure is reproducibly quantitative (12 ZnPPIX/ZnCe6 per 24-mer) based on ZnPPIX or ZnCe6 absorbance and protein analysis (bichinchonic acid assay).

The as-isolated ZnPPIX- or ZnCe6-Bfr typically contains ~40 irons/ZnPPIX-Bfr 24-mer. Iron is incorporated into the as-isolated proteins using the following conditions:

Stock protein solution (0.5 µM 24-mer) in 0.1 M morpholinoethanesulfonic acid (MES) pH 6.5 buffer.
  Stock ferrous ammonium sulfate, 200 mM in water, prepared anaerobically.
  Under anaerobic conditions add 5 µL stock ferrous ammonium sulfate to 1 mL of the ZnPPIX- or ZnCe6-Bfr solution to achieve a mol ratio ~2000 added iron/24-mer.
  Incubate the iron/Bfr solution under anaerobic conditions overnight at 4° C. in the dark.
  Pump air through the protein solution via gentle pipetting, and monitor iron oxidation/incorporation using A340 nm.

no further increase in A340 nm is observed (typically ~2 hr), centrifuge to remove excess iron.

Perform analyses of iron (ferrozine assay) and protein (bichinchonic acid assay) to determine loaded iron-to-protein ratio.

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic sequence

<400> SEQUENCE: 1

Cys Asp Cys Arg Gly Asp Cys Phe Cys
1               5

This procedure typically results in 1000 to 1200 irons loaded per ZnPPIX- or ZnCe6-24-mer. Loading of up to ~3,000 irons per 24-mer can be achieved but results in significant loss of protein.

The solutions used for irradiation and monitoring of iron removal contain ~0.1 uM ZnPPIX-Bfr loaded with 1,000-1,100 iron/24-mer in phosphate-buffered saline pH 7.3 (PBS)+ 10 mM NADH. These solutions are placed in anaerobic 1-cm cuvettes, and irradiated at room temperature with a 300-W tungsten halogen slide projector lamp with the cuvette placed 2 cm from the lens.

Figure 7:
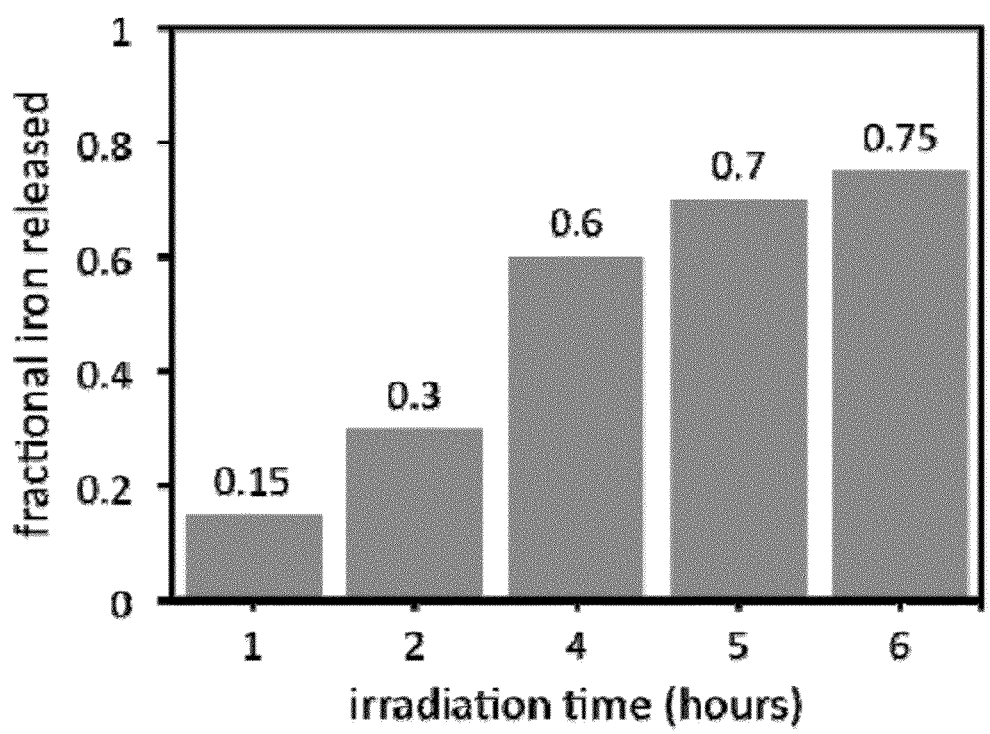
FIG. 7 depicts a graph of the fraction iron released from ZnPPIX-Bfr loaded with ~1,000 irons/24-mer upon irradiation for various amounts of time.

After various irradiation times the cuvettes are transferred to an anaerobic chamber (Coy, Inc.) under low light conditions, and ferrozine is added to the cuvettes to a final concentration of 10 mM. Measurement of the absorbance of the purple ferrozine-iron complex at 562 nm formed immediately upon addition of ferrozine is used to calculate concentrations of released iron. From the known iron concentrations of protein solutions prior to irradiation, the percent of total iron released after irradiation is determined. FIG. 7 depicts the fraction of iron released from ZnPPIX-Bfr loaded with ~1,000 irons/24-mer in PBS pH 7.3+10 mM NADH upon irradiation for various times. Irradiation conditions and ferrozine additions are as described above.

The data in FIG. 7 show that the majority of the iron in the ZnPPIX-Bfr is photo-released within several hours using a relatively crude, non-laser light source and without optimizing the wavelengths of irradiation. It is important to note that no iron is released in the dark (i.e., low light conditions) and that analogous irradiation experiments using iron-loaded Bfr containing heme in place of ZnPPIX showed no iron release. Since heme is not known to be a photosensitizer, these observations show that ZnPPIX is responsible for photosensitizing the iron release from Bfr.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound capable of photo-triggered release of Fenton-reactive iron comprising:
   bacterioferritin;
   one or more tumor targeting peptides and/or tumor specific antibodies coupled to an outer surface of the bacterioferritin, wherein the tumor targeting peptides and/or tumor specific antibodies bind to predetermined cell surface receptors of tumor cells;
   one or more iron-containing molecules disposed in a core of the bacterioferrritin and
   a photosensitizing agent capable of reducing iron when irradiated with activating light coupled to the bacterioferritin, wherein the photosensitizing agent is selected from the group consisting of Zn-protoporphyrin IX and Zn-chlorin e6;
   wherein the photosensitizing agent is positioned at the same site where heme binds in the native bacterioferritin such that when the photosensitizing agent is irradiated with activating light the photosensitizing agent reduces the iron-containing molecules disposed in the core, causing the reduced iron-containing molecules to be released from the core.

2. The compound of claim 1, wherein the compound comprises tumor targeting peptides having the structure CDCRGDCFC (SEQ ID NO. 1).

3. The compound of claim 1, wherein the tumor targeting peptides and/or tumor specific antibodies attached to the bacterioferritin target breast cancer cells.

4. The compound of claim 1, wherein the tumor targeting peptides and/or tumor specific antibodies attached to the bacterioferritin target prostate cancer cells.

5. The compound of claim 1, wherein at least one of the one or more iron containing molecules is ferric-oxyhydroxide polymer.

6. The compound of claim 1, wherein the photosensitizing agent is Zn-chlorin e6.

7. The compound of claim 1, wherein the compound comprises tumor targeting peptides, the tumor targeting peptides being attached to the bacterioferritin and having the structure CDCRGDCFC (SEQ ID NO. 1); the iron containing molecules are ferric-oxyhydroxide polymers; and the photosensitizing agent is Zn-chlorin e6.

8. The compound of claim 1, wherein the photosensitizing agent is Zn-protoporphyrin IX.

* * * * *